Figure 4:
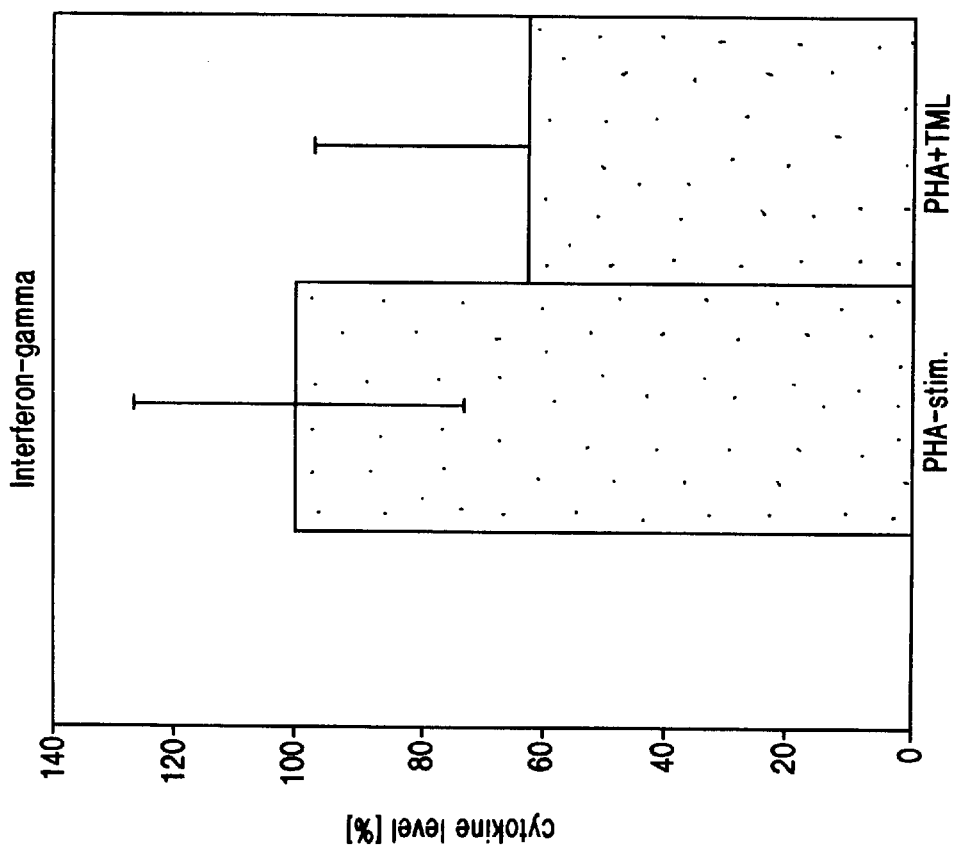
Figure 3:
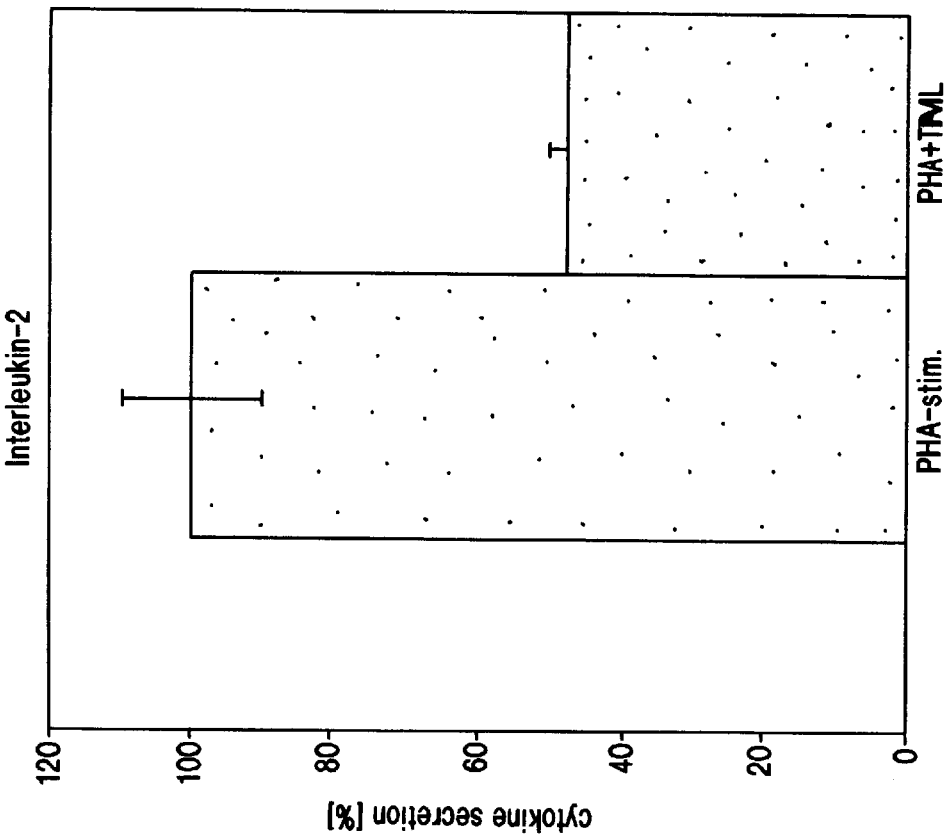
Figure 6:
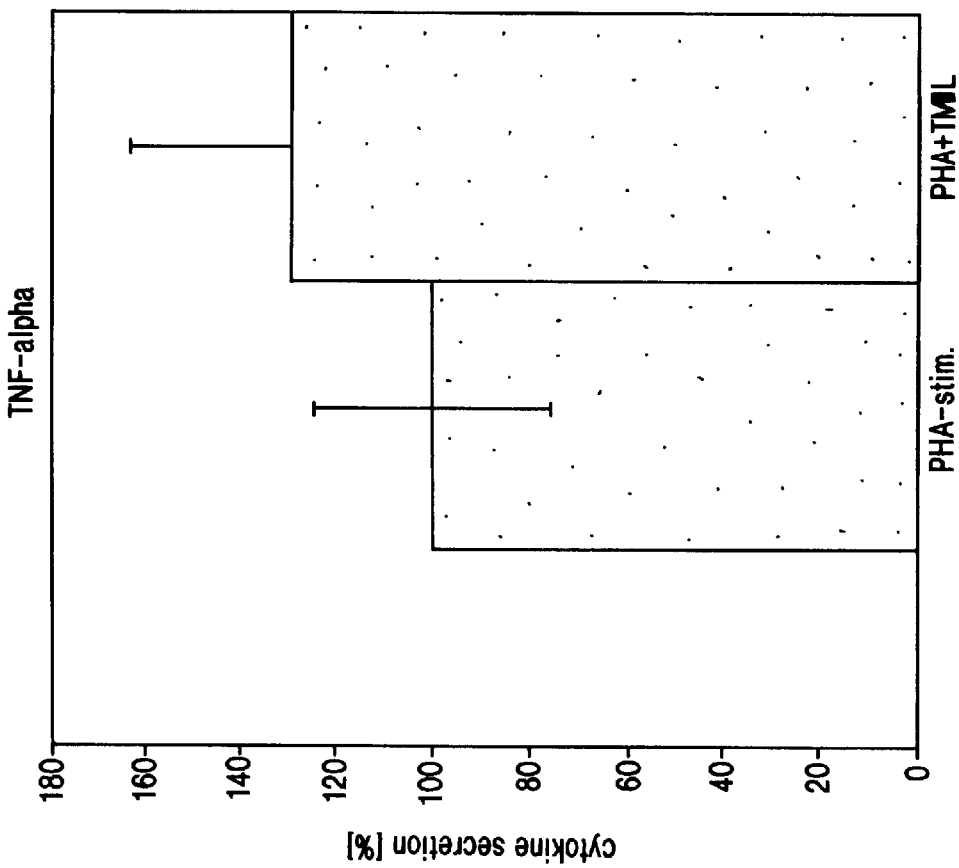

United States Patent [19]
Koch et al.

[11] Patent Number: 6,143,331
[45] Date of Patent: Nov. 7, 2000

[54] PHARMACEUTICAL COMPOSITION WHICH IS STABLE DURING STORAGE AND CONTAINS A THYMUS EXTRACT

[75] Inventors: Susanne Koch, Siegburg; Gerhard Becker, Neckargemünd, both of Germany

[73] Assignee: Sanorell Pharma GmbH & Co., Baiersbronn, Germany

[21] Appl. No.: 09/194,140

[22] PCT Filed: Jun. 3, 1997

[86] PCT No.: PCT/DE97/01142

§ 371 Date: Nov. 25, 1998

§ 102(e) Date: Nov. 25, 1998

[87] PCT Pub. No.: WO97/46245

PCT Pub. Date: Dec. 11, 1997

[30] Foreign Application Priority Data

Jun. 4, 1996 [DE] Germany .................. 196 22 422

[51] Int. Cl.[7] ................................................ A61K 35/26
[52] U.S. Cl. ................. 424/580; 514/2; 514/8; 514/21
[58] Field of Search .................. 424/580; 514/2, 514/8, 21

[56] References Cited

FOREIGN PATENT DOCUMENTS 0 140 134   5/1985   European Pat. Off. .
0 259 564   3/1988   European Pat. Off. .
91 12927    8/1991   WIPO .

OTHER PUBLICATIONS

Database Biosis, Biosciences Information Service, Philadelphia, PA, US; Matthiessen H P et al.: "Low Molecular Mas Inhibitors From Calf Thymus Selective for T–Lymphocyte Proliferation" pp. 1131–1136.

*Primary Examiner*—Leon B. Lankford, Jr.
*Attorney, Agent, or Firm*—Nields & Lemack

[57] ABSTRACT

The invention concerns a process for preparing a pharmaceutical composition of thymus factors which displays immunomodulating and anti-inflammatory properties and is stable during storage. The process comprises the extraction of a homogenized thymus tissue and subsequent repeated ultrafiltration via a filter membrane having an exclusion volume of 30 kD. The resultant first ultrafiltrate is then subjected to a second ultrafiltration process on a membrane having an exclusion volume of 3 kD, the retentate being used. A composition prepared in this way, in contrast to the first ultrafiltrate obtained on leukocyte cultures stimulated by phytohaemagglutinin, displays a great increase in the production of anti-inflammatory IL-10 and a reduction in the formation of inflammation-promoting IL-2 and IFN-gamma.

14 Claims, 5 Drawing Sheets

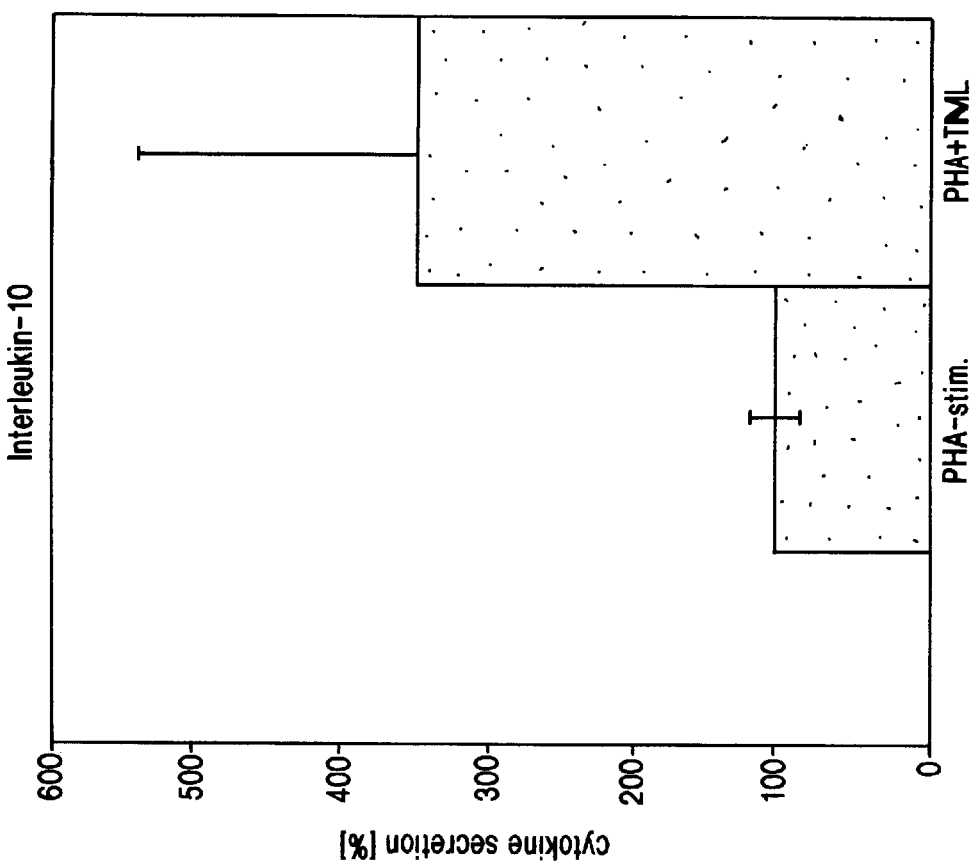
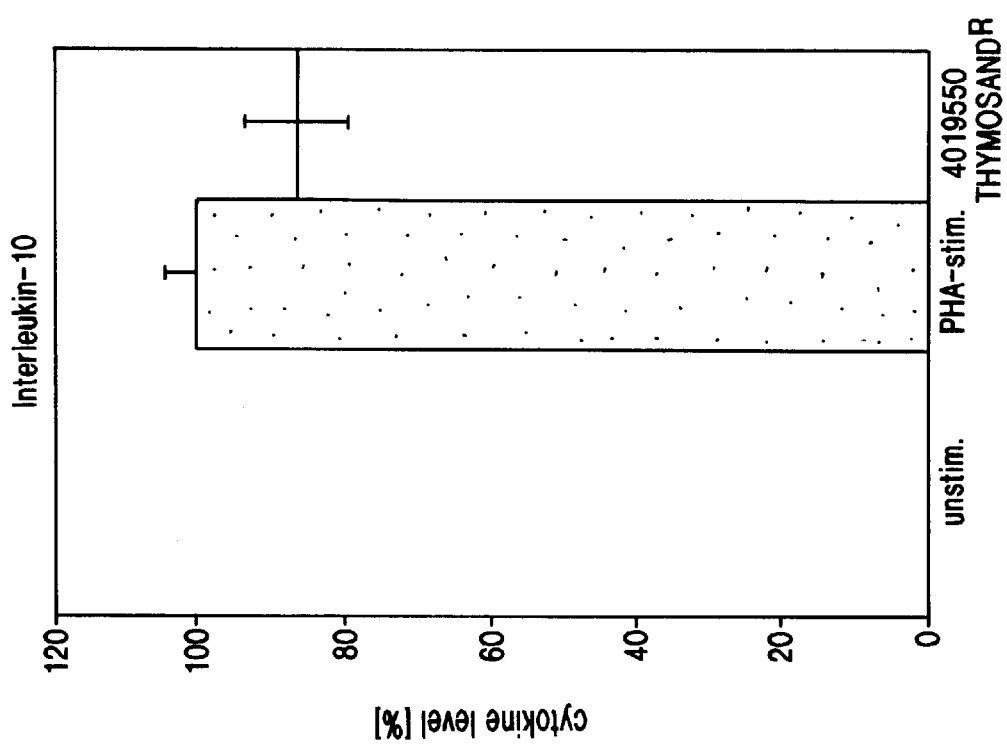

Interleukin-2

Interferon-gamma

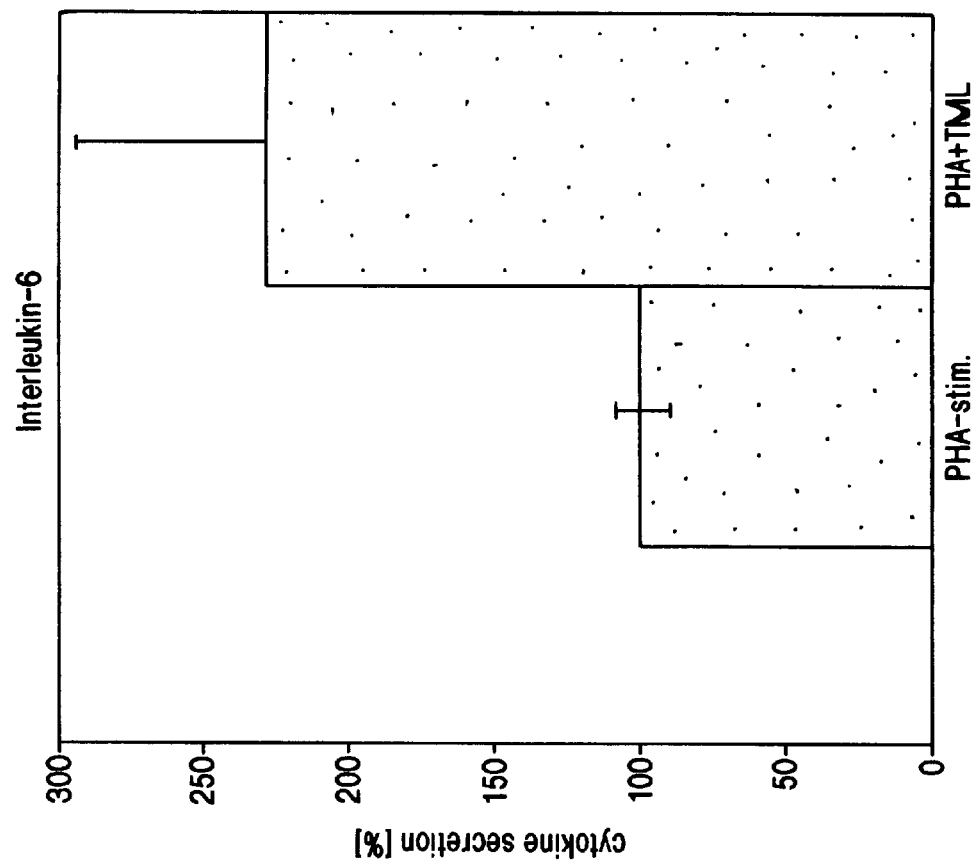
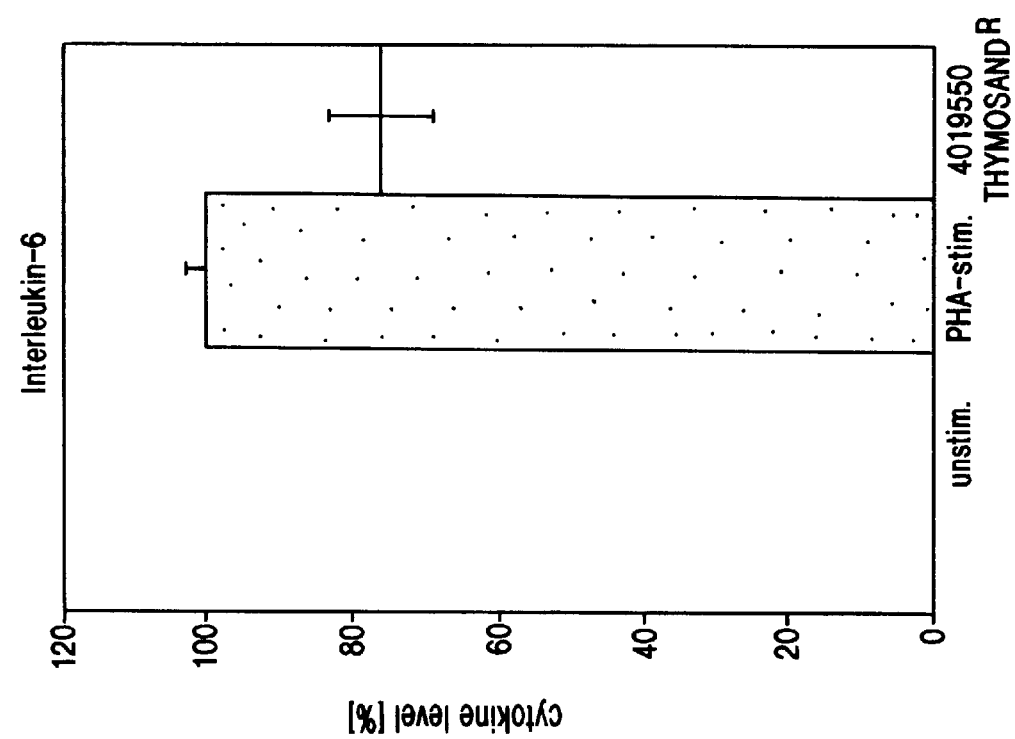

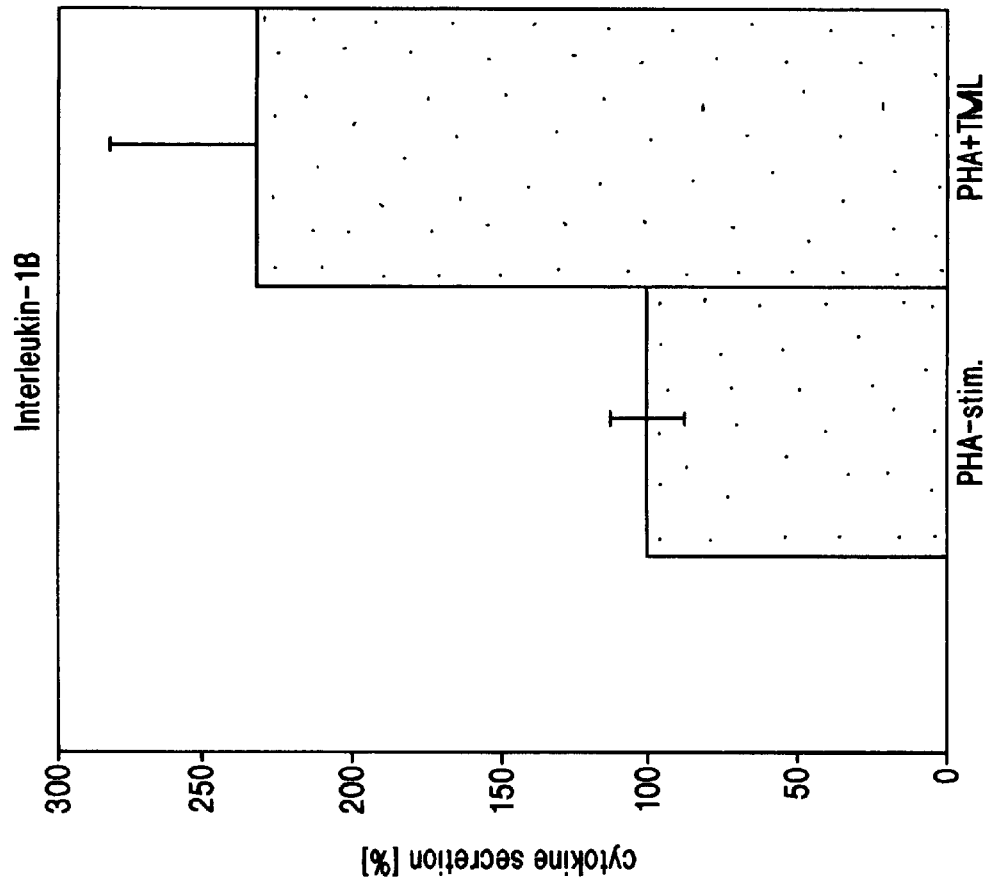
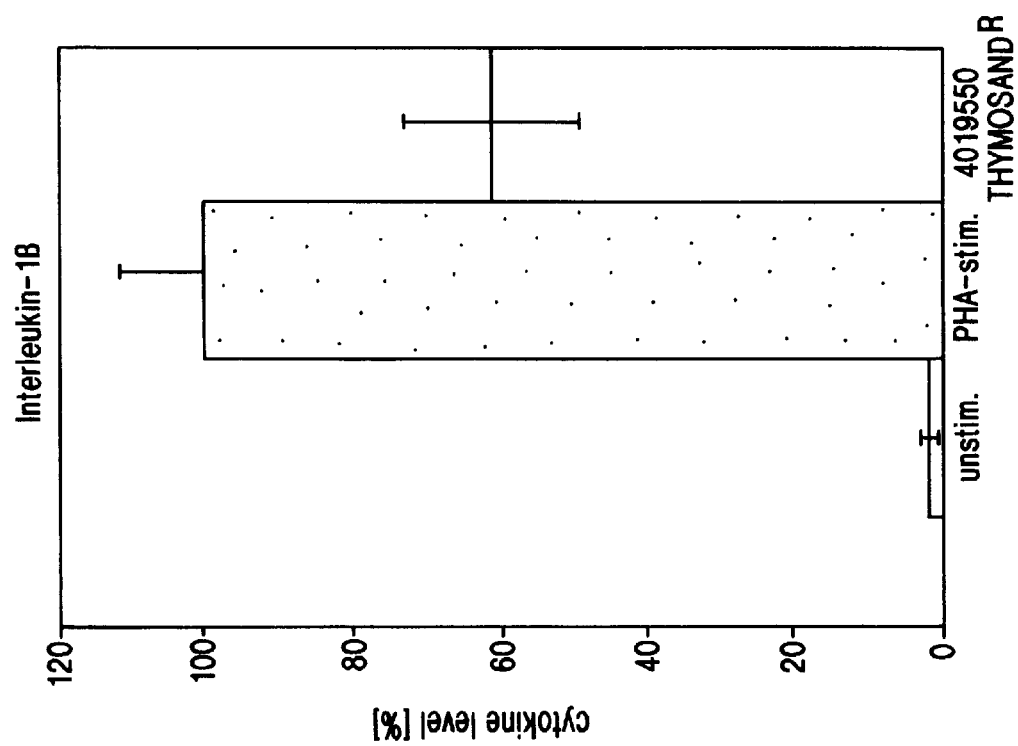

PHARMACEUTICAL COMPOSITION WHICH IS STABLE DURING STORAGE AND CONTAINS A THYMUS EXTRACT

The invention concerns a pharmaceutical composition, which is stable during storage and which can be obtained from a thymus extract and has immunomodulating and inflammation-inhibiting properties.

The production of pharmaceutical preparations from the thymus is known and described from many aspects in the literature. Such extracts contain so-called thymus factors, which comprise peptides produced from thymus. Their structure and function has still not been fully clarified in many cases. However, it is known that thymus factors cause the maturation of T lymphocytes as well as their proliferation by lymph tissue. In addition, it is also known that they play a basic role in the rejection of transplanted tissue as well as in autoimmune diseases. They are thus the subject of intensive investigations.

Thymus factors or peptides are generally called thymosines, of which thymostimulin and thymopoietin, thymosine-$\alpha$-1, thymosine-$\beta$-4 have perhaps been best investigated. It is known, e.g., that thymosine-$\alpha$-1 and thymosine-$\beta$-4 reinforce the antigen presentation to macrophages, for which reason they are also used for the treatment of autoimmune diseases and, among other applications, also in defects in the immune system, such as cancer and allergies.

The preparation and extraction of thymus peptides is known and described, for example, by T. L. K. Low and A. L. Goldstein in "Methods in Enzymology", Vol. 116, p. 213 (1985). In addition, these [products] may also be obtained from sanorell pharma GmbH and Co., Rechtmurgstr. 27, D-72270 Baiersbronn, e.g., under the name Thymosand®.

The storage of aqueous thymus extracts obtained by extraction, however, is limited. Thus, attempts have also been made to synthetically produce pharmaceutically active partial peptides, such as, e.g., the pentapeptide of amino acids 32 to 36 of thymopoietin as well as its analogs (Justus Liebigs Ann. Chem. 1990, 245–247).

The invention thus has the object of making available a pharmaceutically usable mixture of thymus factors, which is stable during storage and which has a pronounced anti-inflammatory effect as well as an immunomodulating action.

This object is now achieved according to the invention in that a thymus tissue homogenized in a way known in and of itself is extracted by means of an aqueous solution, the solid components are separated from the extract and this extract is filtered through an ultrafiltration membrane with an exclusion volume of 30 kD. The process according to the invention is now characterized by the fact that the 30 kD ultrafiltrate that is obtained is subjected to at least one additional filtration on an ultrafilter with an exclusion volume of 3 kD and the retentate is used.

It has been shown surprisingly that a retentate is obtained, which is obviously free of destabilizing factors and which retains its immunomodulating properties, but in addition shows pronounced anti-inflammatory or inflammation-inhibiting properties, by means of an ultrafiltration on a membrane with an exclusion volume of 3000 daltons.

The thymus cells required for the process of the invention are taken from young calves and are rapidly further processed after removal. The preparation of homogenized tissue is known to the person skilled in the art and can be produced, for example, by means of commercially available homogenizers and/or ultrasound treatment. The homogenate is preferably subjected to an autodigestion for at least 10 hours, appropriately at least 20 hours at 2–6° C., usually at 3–5° C. The extraction of the homogenate is conducted by means of water or an aqueous solution, which can be buffered as needed in the neutral or biologically common pH range. The extract thus obtained still contains solid components, which are separated, for example, by means of centrifuging or filtering through filters with appropriately large pores (2.0 $\mu$m, 0.8 $\mu$m, 0.2 $\mu$m). If need be, additional separation or purification steps can be conducted with ammonium sulfate and also other treatments, e.g., with phenol, may be conducted, insofar as these are necessary.

The extract free from the solid components is then subjected to a first ultrafiltration on a membrane with an exclusion volume of 30 kD, whereby preferably hydrophilic membranes, e.g., cellulose and polysulfone membranes, particularly spiral membranes with transverse flow are used. Such membranes are known and are marketed, for example, by the company Amicon under the designation "S1Y30". Preferably this first ultrafiltration step is conducted several times in the process according to the invention, but particularly at least three times, and appropriately at least five times. It has proven appropriate according to the invention to validate the filtration membranes used for this according to the process described in WO 91/12,027 and to check the integrity of the membrane according to WO 93/02,714. In this way, a first ultrafiltrate is obtained, which contains effective thymus factors for medical and biological purposes.

The second ultrafiltration conducted with this ultrafiltrate on the membrane with an exclusion volume of 3 kD is also preferably conducted several times, but particularly at least three times, and preferably at least five times. Preferred ultrafiltration membranes for this second filtration step are, for example, commercially obtainable from the company Amicon under the designation S1Y3. It has also proven appropriate to conduct this latter ultrafiltration step as a so-called diafiltration, i.e., as a repeated filtration, whereby, analogously to a dialysis, undesired components are washed out by multiple filtration with the filtrate solution through the filter. In this way it is possible, without anything further, to separate substances entrained with the extraction solution, such as, for example, buffer salts, and to replace by other additives. It is preferred according to the invention to dilute the retentate concentrated by means of the second ultrafiltration on the 3-kD membrane with a mannitol solution and to repeat the filtration. In this way, the extraction solution can be rebuffered in a simple way. The retentate obtained in this way according to the invention can be lyophilized without anything further while retaining its biological activity.

The invention also concerns a pharmaceutical composition obtained by means of the method described above as well as its use for the production of a pharmaceutical with immunomodulating and anti-inflammatory action, which is stable during storage.

The invention will be explained in more detail on the basis of the following examples.

EXAMPLE 1

A thymus extract, which is commercially obtainable from sanorell pharma GmbH & Co., Rechtmurgstrasse 27, Baiersbronn, Germany under the designation Thymosand®, was used in the following and is denoted below also as UF5. This thymus extract was already ultrafiltered or purified five times by the manufacturer, after removal of the solids, through a validated membrane described in WO 91/12,027

(UF5). This commercially obtainable preparation was then concentrated 10 times (200ml) by means of a concentrator CH2 (obtainable from Amicon, P.O. Box 1103, Witten, Germany), comprising a supply vessel, a hose pump and an ultrafilter mount over an ultrafilter with Delrin head pieces obtained from Amicon under the designation S1Y3. The concentrate obtained in this way was then diluted to five times the volume by means of a 5% mannitol solution and then concentrated again to the original volume. This process was repeated in all five times. The ultrafiltrate was discarded and the retentate containing the thymus peptides in high concentration was subjected to a sterile filtration (0.2 μm) and then lyophilized. The thus-obtained lyophilizate is designated in the following as TML and, in contrast to the initial product, was shown to be extraordinarily stable during storage for several years even at room temperature.

EXAMPLE 2

Solutions with a protein concentration (Lowry method) of 800 μg/ml were prepared from the TML lyophilizate obtained in Example 1 and their biological activity was measured on blood cells according to the process of Hartung et al. (Hartung, T., A. Sauer and A. Wendel, Biochem. Pharmakol. Univ. Konstanz: W. Cytokine response of whole blood; 25$^{th}$ Annual Conference of the Society for Immunology, September 1994; poster). Thus the cytokine release from lymphocytes in batches of whole blood cultures is measured after stimulation with phytohemagglutinin (PHA).

The assay described in this report was conducted with PHA and TML or permeate as costimulators as well as the corresponding negative or positive controls. The cytokines IL-1β, IL-2, IL-6, IL-10; TNF-α and IFN-γ were measured.

Materials and Methods

Blood Collecting: Citrated Blood (Monovette, Sarstedt)
Culture batches: 4-well culture dishes (4×1 ml) with cover (Nunc; Art. No.: 176740)
The culture batches are prepared at the latest 4 hours after blood collecting.
Processing: Specimen Tubes (Sarstedt, Art. No.: 60036550), table centrifuge EBA 3S (Hettich)
Cytokine Measurement: Quantikine Kits (Elisa of R&D Systems GmbH, Borsigstr. 7, 65205 Wiesbaden)
Microplate Photometer HTIII (Anthos)

Production of RPMI medium (under laminar flow): 900 ml of water for injection are placed in a sterilized 2-liter Erlenmeyer flask and a package of powder-form RPMI-1640 (AutoMod, Sigma; Art. No.: R7755) is introduced while stirring. Then 10 ml of a 200 mM L-glutamine solution (Sigma Art. No.: 6–7513) are added.

238.3 mg of HEPES (Sigma; Art. No.: H-0878) are weighed out in a sterilized small glass beaker, dissolved in a small amount of water and added to the RPMI solution. The clear RPMI solution is placed in a sterilized measuring cylinder, which is filled to 1000 ml with water for injection while flushing the RPMI vessel, the small glass beaker and the Erlenmeyer flask. The finished solution is stored in a sterile 1-liter bottle at +4° C. and can be kept for 1 month.

Preparation of RMPI medium+PHA (under laminar flow): 1.875 mg of PHA (Sigma; Art. No.: L9132) is weighed out in a sterilized 100-ml measuring flask and filled with RPMI medium up to the calibration mark. The solution is stirred thoroughly for a short time, divided into 30-ml aliquots in sterilized 30-ml vials provided with sterile stoppers and sealing pieces. Removal is conducted with sterile disposable syringes or cannula.

Preparing the whole-blood batches under laminar flow: 4-well culture dishes are used. The final concentrations are the following: PHA, 15 μg/ml, TML 806 μg/ml and UF5/Thymosand®, 50 μg/ml. The culture batches individually are comprised of the following components (relative to 1 well of the culture dish), which are pipetted directly into the wells of the culture dishes.

| | |
|---|---|
| Negative controls - | 200 μl of blood, 522 μl of medium, 278 μl of PBS or mannitol |
| Positive controls - | 200 μl of blood, 522 μl of medium + PHA, 278 μl of mannitol solution ("stimulates/mannitol volumetric equilibration") |
| TML sample - | 200 μl of blood, 522 μl of medium + PHA, 278 μl of TML ("stimulates + TML") |
| Thymosand ® specimen - | 200 μl of blood, 522 μl of medium + PHA, 278 μl of Thymosand ® (lot no. 4019550) |

The batches are incubated for 24 h in the culture dishes with closed cover in the incubation chamber at +37° C. in an atmosphere containing $CO_2$.

Working up the Culture Batches:

The blood specimens are centrifuged in order to obtain the serum supernatants (10 min; 5600 rpm), made up into aliquots in marked sample tubes of up to 410 μl, each and stored at −70° C.

Conducting the Cytokine Determination

The cytokines IL-1β, 1L-2, IL-6, IL-10, TNF-α and IFN-γ were determined according to the test instructions of the manufacturer R&D Systems, from the serum supernatants. Double determinations were conducted for each measurement. In order to obtain statistically valid values, 3 determinations were made for each cytokine, each time with a new standard series, so that 6 measurement values resulted for each sample per cytokine (with the exception of IL-2).

The results can be derived from the accompanying FIGS. 1–10.

Figure 5:
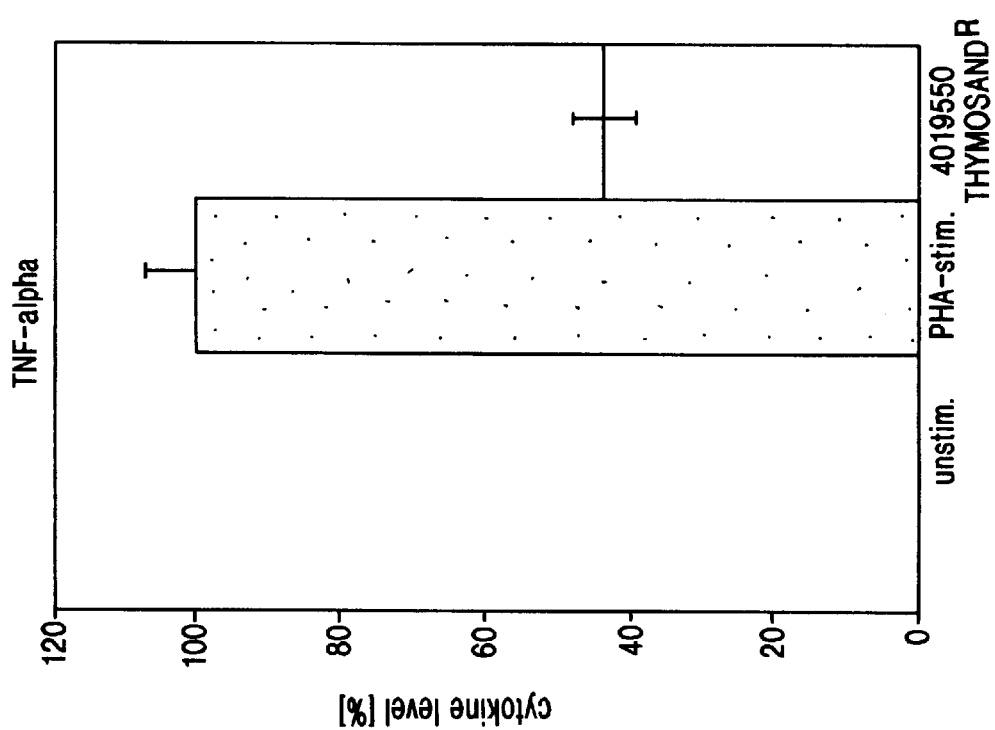

Phytohemagglutinin is used as a synthetic agent, which simulates a fever reaction in cell cultures. As is visible from the figures, the presence of phytohemagglutinin in all cases causes an increase of the cytokine level. The retentate TML obtained according to the invention produces a pronounced increase of interleukin-10 production (IL-10) on lymphocytes in the PHA-stimulated cell culture (FIG. 2), which corresponds to an inflammation-inhibiting effect, since IL-10 inhibits prostaglandin-E2 synthesis. In contrast to this, the formation of proinflammatory interleukin-2 (IL-2) (FIG. 4) as well as also of proinflammatory IFN-gamma (FIG. 3) is reduced on PHA-stimulated leukocytes. The composition filtered only through a 30-kD membrane, but not through a 3-kD membrane (UF5/Thymosand®) causes a reduction of interleukin-10 production (FIG. 1). The secretion of TNF-α is increased by the TML fraction still further to approximately 130% (FIG. 6), whereas the Thymosand® fraction that is not free of its low-molecular components causes a reduction of TNF-α secretion on PHA-stimulated cells to approximately 45% (FIG. 5).

The secretion of IL-6 is increased to approximately 230% by TML, while on the other hand, Thymosand® (UF5) causes a decrease to approximately 75% (FIGS. 7 and 8).

The secretion of interleukin-1β is increased to approximately 230% by the TML fraction (TML retentate) (FIG. 10), while the IL-1β secretion, in contrast, decreases to 60% with the UF5 preparation (Thymosand®) (FIG. 9).

This result is rather surprising, since the quantity ratios of the individual peptide fractions or thymus factors in the TML do not differ in comparison to the Thymosand® initial product.

A composition is obtained with the process according to the invention, which remains stable for years, even at room temperature, and can be prepared with high concentrations (up to 100 times those of Thymosand®).

What is claimed is:

1. Process for the production of a pharmaceutical composition of thymus factors with immunomodulating and inflammation-inhibiting properties comprising the extraction of a homogenized thymus tissue by means of an aqueous solution, separating the solid components of the extract, and at least one first ultrafiltration of the extract through a filter membrane with an exclusion volume of 30 kD in order to obtain a first ultrafiltrate, said first ultrafiltrate being subjected to at least one additional second filtration through an ultrafilter with an exclusion volume of 3 kD to form a retentate.

2. Process according to claim 1, further characterized in that the retentate is mixed with an aqueous mannitol solution and is diafiltered at least once on an ultrafilter with an exclusion volume of 3 kD.

3. Process according to claim 2, further characterized in that the diafiltration is conducted three to seven times with mannitol.

4. Process according to claim 1 or 2, further characterized in that the first ultrafiltration is conducted three to seven times on the filter with the exclusion volume of 30 kD.

5. Process according to claim 4, wherein the diafiltration is conducted three to seven times with mannitol.

6. Process according to claim 4, wherein said solid components are removed by means of a filter with pore size 1 to 3 μm.

7. Process according to claim 4, wherein the filter for the first ultrafiltration is validated by means of the Leviviridae virus.

8. Process according to claim 4, wherein there is only one second filtration, and wherein said retentate obtained in said one second ultrafiltration is lyophilized.

9. Process according to claim 1 or 2, wherein said solid components are removed by means of a filter with pore size 1 to 3 μm.

10. Process according to claim 1 or 2, wherein the filter for the first ultrafiltration is validated by means of the Leviviridae virus.

11. Process according to claim 1 or 2, wherein there is only one second filtration, and wherein said retentate obtained in said one second ultrafiltration is lyophilized.

12. Pharmaceutical preparation comprising said retentate prepared by the process of claim 1 or 2.

13. Process according to claim 1 or 2, wherein there are a plurality of second filtrations, and wherein said retentate obtained after completion of said plurality is lyophilized.

14. A method of treating a warm-blooded animal having a condition requiring immunomodulating action or anti-inflammatory action, comprising administering to said warm-blooded animal an effective amount of a pharmaceutical composition of thymus factors, said pharmaceutical composition being prepared by the extraction of a homogenized thymus tissue by means of an aqueous solution, separating the solid components of the extract, and at least one first ultrafiltration of the extract through a filter membrane with an exclusion volume of 30 kD in order to obtain a first ultrafiltrate, wherein the first ultrafiltrate is subjected to at least one additional second filtration through an ultrafilter with an exclusion volume of 3 kD to obtain retentate comprising said thymus factors.

* * * * *